United States Patent [19]

Tensmeyer

[11] 3,955,921

[45] May 11, 1976

[54] METHOD OF KILLING MICROORGANISMS IN THE INSIDE OF A CONTAINER UTILIZING A LASER BEAM INDUCED PLASMA

[75] Inventor: Lowell G. Tensmeyer, Indianapolis, Ind.

[73] Assignee: Eli Lilly and Company, Indianapolis, Ind.

[22] Filed: Oct. 15, 1974

[21] Appl. No.: 514,673

Related U.S. Application Data

[63] Continuation-in-part of Ser. No. 290,303, Sept. 19, 1972, abandoned.

[52] U.S. Cl. ........................ 21/54 R; 219/121 LM
[51] Int. Cl.² ........................................... A61L 1/00
[58] Field of Search ............... 21/54 R, 102 R; 204/DIG. 11; 331/94.5 A; 219/121 P, 121 L, 121 LM; 426/236, 320

[56] References Cited

UNITED STATES PATENTS 3,383,163   5/1968   Menashi ........................... 21/54 R

OTHER PUBLICATIONS

Meyerand, *AIAA Journal*, Vol. 5(10); pp. 1730–1733 (1967).

*Primary Examiner*—Joseph Scovronek
*Assistant Examiner*—Timothy W. Hagan
*Attorney, Agent, or Firm*—Ralph W. Ernsberger; Everet F. Smith

[57]   ABSTRACT

Novel method of killing microorganisms in the inside of a container comprising repeatedly sparking a focused, ultra-short-pulsed laser beam in the inside thereof.

7 Claims, No Drawings

METHOD OF KILLING MICROORGANISMS IN THE INSIDE OF A CONTAINER UTILIZING A LASER BEAM INDUCED PLASMA

CROSS-REFERENCE

This patent application is a continuation-in-part of pending patent application, Ser. No. 290,303, filed Sept. 19, 1972 now abandoned.

BACKGROUND OF THE INVENTION

1. Field of the Invention

This invention relates to a method of killing microorganisms in the inside of a container. More particularly, this invention relates to a method of killing microorganisms by repeatedly sparking a focused, ultra-short-pulsed laser beam in the inside of such a container.

2. Description of the Prior Art

Killing of microorganisms, which when carried to totality constitutes sterilization, in containers into which are filled such substances as parenteral medications, foods, beverages, dairy products, and the like, has been practised for decades for the purpose of preventing the transmission of disease. Many methods have been devised to accomplish this purpose. Heat, both dry and wet, has been a popular method of killing microorganisms in the food, beverage and pharmaceutical arts for a long time. The use of chemicals such as formaldehyde, phenol, ethanol, ethylene oxide, and the like for killing microorganisms has found many useful applications. More recently irradiation, such as beta, gamma, and ultraviolet rays have been employed in specialized applications for killing microorganisms.

In 1968, U.S. Pat. No. 3,383,163 described a method of sterilizing the surface of a material which does not conduct electricity comprising contacting such surface with a gaseous plasma at an extremely high temperature. In this method a corona discharge was utilized to generate a plasma inside a container. The corona discharge was achieved by introducing a grounded electrode into the container, surrounding the container with a coil and pulsing from about 5000 to about 7000 volts and above into the coil. Exposure of the surface to a plasma for a very brief period of time, normally not longer than one-tenth of a second, is described.

In the time since U.S. Pat. No. 3,383,163 was issued, many attempts have been made to develop the plasma sterilization process into an economically feasible method because of the inherent advantage of killing the microorganisms in the inside of a container just prior to filling. However, the mechanical problems associated with introducing a grounded electrode into a container and simultaneously surrounding the container with a high voltage coil have been found to be of such a magnitude as to defeat exploitation of the invention. Moreover, the volume of plasma generated by the corona discharge is dependent on the style and shielding of the electrode tip, the winding of the high voltage coil and the potential difference between said electrode and said coil at the moment of the pulsed discharge, and such requirements have presented problems in the location of the electrode and coil so as to fill the container with plasma. Furthermore, the voltage required to initiate the corona discharge is substantial and requires specialized electrical circuitry.

Accordingly it is an object of this invention to provide a method of killing microorganisms in the inside of a container with a plasma which can be generated without the requirement for the mechanical introduction of an element into said container and the surrounding of said container with any element associated with said method.

Another object of this invention is to accomplish the killing of microorganisms in the inside of a container by generating a plasma in the inside of said container, said plasma not being required to contact the inside surfaces of said container to effect the microorganism kill.

Yet another object of the instant invention is to provide a method of killing microorganisms in the inside of a container irrespective of the electrical conducting properties of said container, by generating a plasma in the inside of said container.

Still another object of this invention is to kill microorganisms in the inside of a container by the repeated production of plasmas in the inside of said container.

SUMMARY

It has now been discovered that repeatedly sparking a focused, ultra-short-pulsed laser beam inside a container accrues an accumulated plasma existence time which is effective in killing microorganisms in the inside of said container, said plasma being produced in the region of the focal point of said beam.

DESCRIPTION OF THE PREFERRED EMBODIMENTS

The novel method of killing microorganisms in the inside of a container comprises repeatedly sparking a focused, ultra-short-pulsed laser beam inside of said container, said spark being achieved by focusing said beam to a point of convergence (focal point) inside of said container.

The focused, ultra-short-pulsed laser beam is achieved by Q-switching or mode-locking a laser beam, each pulse having a duration of from about one-tenth to about 300 nanoseconds. The mechanics and methods of Q-switching and mode-locking laser beams to produce pulsed beams of ultra short duration are old and well known to those skilled in the art, and constitute no part of the instant invention.

The mechanics and methods of generating a spark by focusing an ultra-short-pulsed laser beam at a focal point where the cone of said beam converges are also well known to those skilled in the art. Optics appropriate to the wave length are employed in focusing an ultra-short-pulsed laser beam. The focal point of the cone of the ultra-shot-pulsed laser beam must be sufficiently short to assure the generation of a spark on each pulse. Such focal point is a function of the energy in said beam; there being a direct relationship between the beam energy and the maximum focal point distance which unfailingly achieves a spark with each pulse. The maximum focal length can be increased by increasing the energy in the beam.

The instant invention does not depend on the energy in the beam, but rather the generation of a spark at the focal point. Any ultra-short-pulsed laser beam which will spark at its focal point when such focal point is located within the inside of a container will effectively kill microorganisms in the inside of said container with repeated sparkings. It will be understood that it is a function of the mechanics of an installation in which the inside of containers are sterilized to coordinate the positioning of the optics which are employed to focus the ultra-short-pulsed laser beam with the beam energy which will produce a spark at the focal point of said beam located inside of said containers.

A laser beam can be focused through a material that is optically clear and which does not appreciably distort the converging cone of the beam. So it is possible to accomplish the killing of microorganisms on the inside of a container in which there is no opening by focusing a laser beam through the material of which the container is made if such material meets the criteria described above. However, the greater number of the containers in which microorganisms will be killed by the useful method of this invention will be made of materials which do not meet the criteria noted above. Consequently, it is preferable that the containers, in which microorganisms will be killed by the novel process of the present invention, have an opening therein, and that the ultra-short-pulsed laser beam be focused through such opening.

Consequently, the size of the opening in the container must be considered in designing a beam and the focusing thereof as a partial distortion of the converging sides of the cone of said focused beam by a contact with the material of which the container is made can corrupt said beam and interrupt the sparking thereof.

It is generally accepted that the spark of a focused, ultra-short-pulsed laser beam is a "plasma". In the instant invention "plasma" defines a highly or essentially completely ionized body of gas which is composed of positively charged nuclei and negatively charged electrons, and exists at an extremely high temperature, perhaps approaching that of the sun. The life of the spark of a focused, ultra-short-pulsed laser beam is of exceptionally short duration, being in the neighborhood of from about 5 nanoseconds to about 5 microseconds.

While the exact mechanism by which the spark of a focused, ultra-short-pulsed laser beam accomplishes the killing of microorganisms in the inside of a container in which said spark occurs is not known, it is known that it is not necessary that the inside surfaces of said container be contacted by said spark.

The plasma which is the result of the ionization of the gas inside said container by the focused, ultra-short-pulsed laser beam spark can be formed from many ionizable gases. Air, comprised of nitrogen and oxygen, will form a plasma. Other ionizable diatomic gases, such as the halogens, will form plasmas, however, the preferred gases for plasma formation are monatomic gases such as argon, helium, xenon, neon, and the like. Irrespective of the gas utilized, the generation of a spark from a focused, ultra-short-pulsed laser beam within the body of said gas constitutes the formation of a plasma.

In a preferred embodiment of the instant invention, a monatomic gas is introduced into the container, in which microorganisms are to be killed, prior to the generation of a plasma in said container. The monatomic gases are easier to ionize than oxygen or nitrogen; consequently, less energy is required to generate a plasma. An especially preferred embodiment constitutes the introduction of argon into the container prior to the generation of a plasma therein because such gas is plentiful and economic, and the residue thereof is limited to neutral argon.

Furthermore, plasmas can be formed from ionizable gases when the pressure within said container, wherein said focused, ultra-shot-pulsed laser spark is generated, is other than atmospheric. The pressure can be either sub- or super-atmospheric. And again, regardless of the pressure of the ionizable gas, the generation of a focused, ultra-short-pulsed laser beam spark constitutes a plasma, which in turn is effective in killing microorganisms in the inside of a container, when such spark is generated therein.

The key to killing microorganisms in the inside of a container by sparking a focused, ultra-short-pulsed laser beam therein lies in the total accumulated duration of the spark and the integrated intensity thereof from a focused, ultra-short-pulsed laser beam. As was denoted hereinbefore, the duration of a single ultra-short-pulse of a laser beam can range between about one-tenth and about 300 nanoseconds. And the spark, generated therefrom by the focusing of said beam, exists for from about 5 nanoseconds to about 5 microseconds. The total elapsed duration of the spark required to achieve the killing of microorganisms in the inside of a container wherein said spark is generated by a focused, ultra-short-pulsed laser beam varies with the surface of the container and the microorganisms to be killed. The electrical conducting properties of the material of which the container is constructed is of no moment, as the plasma is generated by forces entirely within the confines of the container; no elements external thereto being required. Therefore, microorganisms can be killed in the inside of metal containers as readily as with glass, ceramic, or plastic bodies. Generally, a single spark is insufficient to achieve a significant measure of microorganism kill. A multiple of repeating sparks does, however, accomplish the killing of microorganism. It has been found that as few as one-hundred sparks will accrue a sufficient total accumulated duration of plasma existence to materially alter the viability of microorganisms which are inside a container in which a focused, ultra-short-pulsed laser beam is sparked.

The effect of the repeated sparking of a focused, ultra-short-pulsed laser beam is cumulative. When from about 100 to about 10,000 consecutive focused, ultra-short-pulses are sparked within a container, total killing of the microorganisms in the inside of said container is accomplished. These 100 to 10,000 sparks result in a total accumulated duration of plasma existence from about 1 microsecond to about 50 milliseconds.

Inasmuch as the temperature of the plasma resulting from the sparking of the focused, ultra-short-pulsed laser beam is momentarily near that of the sun, it is preferred that the total accumulated duration of the plasma be held to the minimum consistent with the total killing of the microorganisms in the inside of the container. Moreover, inasmuch as the sparking of the focused, ultra-short-pulsed laser beam can be likened to a sonic boom, it is imperative that the focal point of the ultra-short-pulsed laser beam be located at a sufficient distance from any point or part of the inside of said container to avoid the contacting of said inside surface by the plasma.

Typical containers in which the microorganisms present therein can be killed by sparking a focused, ultra-short-pulsed laser beam inside thereof are ampoules and vials used for parenteral medications, beverage bottles and cans such as those used for soft drinks, beer and ale, orange and lemon concentrates, and the like, milk bottles and cartons, baby food jars and cans and canned food containers, and the like.

This invention is further illustrated by the following example.

EXAMPLE I

This experiment was run to determine the effect of repeatedly sparking a focused, ultra-short-pulsed laser beam inside a container on the bacterial count within said container.

Forty-five 10 ml. vials having a 0.5 inch neck opening were each inoculated with 0.1 ml. of a 1000 spores/ml. suspension of *Bacillus subtilis*. The *B. subtilis* was suspended in water. After inoculation, each vial was swirled to distribute the *B. subtilis* suspension evenly on the inside surface and up onto the shoulder of the vials. Then the inoculated vials were dried at about 35° C. for about 24 hours.

After drying, the innoculated vials were divided into nine groups of five bottles each. A focused, ultra-short-pulsed laser beam producing a spark having a duration of about 15 nanoseconds was repeatedly sparked inside four of the five vials in each group. The number of repeated sparkings was varied from group to group. The fifth vial in each group was utilized as a control vial. The number of sparkings ranged from 5 to 1600 with each of the four vials in each group being subjected to same number of sparks.

After the vials had been exposed to the sparkings from the focused, ultra-short-pulsed laser beam, five ml. of water were added to each vial, and the vial swirled to aid in suspending the remaining viable *B. subtilis* spores in the water. Then a 1.0 ml. aliquot was removed from each vial and placed in a petri dish. About 15 ml. of a soybean - casein digest agar were added to each petri dish and the dish swirled to mix the sample and the agar. The thus prepared petri dishes were incubated at 35° C. for 48 hours and a bacterial count made on each. Table No. 1 shows the viable organisms per vial calculated by multiplying the bacterial count from each petri dish by five to reflect the 1 to 5 aliquot taken as a sample. The data show that the effect of sparking a focused, ultra-short-pulsed laser beam inside the vials is a reduction of viable organisms within the vial; the larger the number of repeated sparkings, the fewer the number of viable *B. subtilis* organisms remaining.

TABLE I

Effect of Repeated Sparkings of a Focused, Ultra-Short-Pulsed Laser Beam Inside a 10 ml. Vial Inoculated With B. Subtilis Organisms, Each Spark Having a Duration of About 15 Nanoseconds In.Air

| Vial No. | No. of Repeated Sparkings of Focused, Ultra-Short-Pulsed Laser Beam | Total Exposure time in Microseconds | Number of Viable B. subtilis Organisms Remaining in Vial after Exposure | Average of Number of Viable B. Subtilis Organisms per Group of Four Vials |
|---|---|---|---|---|
| 1 | 5 | 0.075 | 300 | |
| 2 | 5 | 0.075 | 125 | |
| 3 | 5 | 0.075 | 150 | 195 |
| 4 | 5 | 0.075 | 200 | |
| 5 | None | None | 200 | |
| 6 | 10 | 0.150 | 40 | |
| 7 | 10 | 0.150 | 60 | |
| 8 | 10 | 0.150 | 60 | 60 |
| 9 | 10 | 0.150 | 60 | |
| 10 | None | None | 80 | |
| 11 | 20 | 0.3 | 75 | |
| 12 | 20 | 0.3 | 60 | |
| 13 | 20 | 0.3 | 100 | 66 |
| 14 | 20 | 0.3 | 20 | |
| 15 | None | None | 80 | |
| 16 | 40 | 0.6 | 60 | |
| 17 | 40 | 0.6 | 40 | |
| 18 | 40 | 0.6 | 100 | 66 |
| 19 | 40 | 0.6 | 60 | |
| 20 | None | None | 75 | |
| 21 | 100 | 1.5 | 60 | |
| 22 | 100 | 1.5 | 20 | |
| 23 | 100 | 1.5 | 35 | 31 |
| 24 | 100 | 1.5 | 15 | |
| 25 | None | None | 25 | |
| 26 | 200 | 3.0 | 30 | |
| 27 | 200 | 3.0 | 80 | |
| 28 | 200 | 3.0 | 60 | 45 |
| 29 | 200 | 3.0 | 10 | |
| 30 | None | None | 90 | |
| 31 | 400 | 6.0 | 25 | |
| 32 | 400 | 6.0 | 25 | |
| 33 | 400 | 6.0 | 10 | 15 |
| 34 | 400 | 6.0 | 10 | |
| 35 | None | None | 90 | |
| 36 | 800 | 12.0 | 20 | |
| 37 | 800 | 12.0 | 10 | |
| 38 | 800 | 12.0 | 0 | 9 |
| 39 | 800 | 12.0 | 5 | |
| 40 | None | None | 70 | |
| 41 | 1600 | 24.0 | 0 | |
| 42 | 1600 | 24.0 | 15 | |
| 43 | 1600 | 24.0 | 5 | 6 |
| 44 | 1600 | 24 | 5 | |
| 45 | None | None | 60 | |

What is claimed is:

1. The method of killing microorganisms in the inside of a container having an opening therein comprising directing a focused ultra-short-pulsed laser beam through said opening to a focal point in the inside of said container, said focal point being at a sufficient distance from the inside surface of said container to avoid contacting said surface with the spark resulting from the convergence of said laser beam at said focal point thereof, and generating a continuous succession of individual ultra-short-lived plasmas in the inside of said container by repeatedly sparking said laser beam therein, said individual plasmas having an accumulated life of from about one microsecond to about 50 milliseconds.

2. A method according to claim 1 wherein each individual plasma has a duration of from about 5 nanoseconds to about 5 microseconds.

3. A method according to claim 2 wherein each individual plasma is generated by a focused laser beam pulse of from about one-tenth to about 300 nanoseconds.

4. A method according to claim 1 wherein the total accumulated plasma life is the product of from about 100 to about 10,000 successive ultra-short pulses of said laser beam, each of said pulses producing an individual plasma.

5. The method of killing microorganisms in the inside of a container having an opening therein comprising:
 a. introducing a monatomic gas into said container through said opening;
 b. directing a focused ultra-short-pulsed laser beam through said opening to a focal point in the inside of said container, said focal point being at a sufficient distance from the inside surface of said container to avoid contacting said surface with the spark resulting from the convergence of said laser beam at said focal point thereof;
 c. generating a continuous succession of ultra-short-lived plasmas in the inside of said container by repeatedly sparking said laser beam therein; and
 d. exposing the inside of said container to a total accumulated plasma existence of from about one microsecond to about 50 milliseconds.

6. The method of killing microorganisms in the inside of a container having an opening therein comprising generating a continuous succession of individual plasmas therein by repeatedly sparking a focused ultra-short-pulsed laser beam therein, said beam being focused through said opening in said container, said beam converging at a focal point sufficiently distant from the inside surface of said container to avoid contacting said surface with the spark resulting from said convergence.

7. The method of killing microorganisms in the inside of a container having optically clear walls comprising directing a focused ultra-short-pulsed laser beam to a focal point in the inside of said container and at a distance from the inside surface thereof which avoids contacting said surface with the spark resulting from the convergence of said beam at the focal point thereof and generating a continuous succession of individual plasmas in the inside of said container by repeatedly sparking said laser beam therein.

* * * * *